United States Patent [19]

Pitt et al.

[11] Patent Number: 4,968,599
[45] Date of Patent: Nov. 6, 1990

[54] PHOTOGRAPHIC COMPOSITION CONTAINING A FLUORINATED SULFOSUCCINATE

[75] Inventors: Alan R. Pitt, St. Albans; Trevor J. Wear, Stanmore, both of United Kingdom

[73] Assignee: Eastman Kodak Company, Rochester, N.Y.

[21] Appl. No.: 374,400

[22] Filed: Jun. 29, 1989

Related U.S. Application Data

[63] Continuation of Ser. No. 162,782, Mar. 2, 1988, abandoned.

[30] Foreign Application Priority Data

Mar. 24, 1987 [GB] United Kingdom ............... 8707032

[51] Int. Cl.$^5$ ............................................. G03C 1/02
[52] U.S. Cl. ............................ 430/631; 430/527; 430/528; 560/149; 560/150
[58] Field of Search ............ 430/631, 527, 528; 560/149, 150

[56] References Cited

U.S. PATENT DOCUMENTS 4,347,308 8/1982 Takeuchi et al. .
4,385,110 5/1983 Yoneyama et al. .
4,547,459 10/1985 Kamio et al. ............... 430/631

FOREIGN PATENT DOCUMENTS 9046733 3/1972 Japan .

*Primary Examiner*—Jack P. Brammer
*Attorney, Agent, or Firm*—Paul A. Leipold

[57] ABSTRACT

Fluoroalkyl surface active agents are provided as effective coating aids for hydrophilic colloid coating compositions for photographic materials. These coating aids are of the formula:

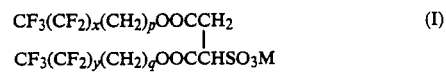

$$CF_3(CF_2)_x(CH_2)_p OOCCH_2 \atop CF_3(CF_2)_y(CH_2)_q OOCCHSO_3M \qquad (I)$$

where
M is a cation,
x and y are each independently 0 or an integer of from 1 to 6 such that the sum of x and y is an integer of from 2 to 6, and
p and q are each independently 1 or 2, with the proviso that when the sum of x and y is 6, p and q are each 1, and when the sum of x and y is 2, p and q are each 2.

8 Claims, No Drawings

PHOTOGRAPHIC COMPOSITION CONTAINING A FLUORINATED SULFOSUCCINATE

This is a continuation of application Ser. No. 162,782, filed Mar. 2, 1988, now abandoned.

FIELD OF THE INVENTION

The present invention relates to photographic compositions and elements having fluorinated sulfosuccinated compounds as coating aids.

BACKGROUND OF THE INVENTION

In the preparation of a photographic material, a support is usually coated with one or more layers comprising an aqueous solution of a hydrophilic colloid binder, such as gelatin. Such layers include, for example, silver halide emulsion layers, intermediate layers, antihalation layers, filter layers, antistatic layers, protective layers, and the like. For multilayer materials, the layers may be coated simultaneously, as described in U.S. Pat. Nos. 2,761,791 and 3,508,947.

In the preparation of hydrophilic colloid layers, the coating solutions must be coated uniformly with a minimum of repellency spots, or repellencies. A repellency is a coating unevenness, such as a round, oval, or comet-shaped indentation or crater in the layer or layers. Repellencies are often caused by the presence in the coating composition of finely-divided insoluble materials in the form of addenda, impurities, or contaminants that are surface active. Solutions coated in the preparation of photographic materials often contain dispersed insoluble photographic addenda, such as organic solvents, or addenda to alter certain physical properties, such as lubricants. Many of these addenda are capable of imparting repellencies to coated layers.

Photographic gelatin may contain insoluble residues of certain naturally-occurring animal fats and fatty acids, which can impart repellencies to the coated layer. Also, surface active contaminants may be introduced from external sources during preparation of the coating composition or during coating. For example, a layer may be contaminated during or immediately after coating by various oils used to lubricate the coating apparatus.

A wide variety of surface active agents have been suggested for use as coating aids to control the uniformity of photographic layers. For example, Japanese Kokai No. 49/046733 describes the use of certain fluoroalkyl sulfosuccinates as coating aids for photographic materials. These compounds, however, often do not prevent repellencies caused by surface active materials having low surface tension properties, such as silicone fluids used as lubricants and sealants.

It would therefore be highly desirable to provide a coating aid for photographic compositions that effectively reduce repellencies, especially those caused by materials from external sources, such as silicone fluids used as lubricants and sealants.

SUMMARY OF THE INVENTION

The present invention provides a photographic composition comprising a hydrophilic colloid binder and a fluoroalkyl surface active agent having the formula:

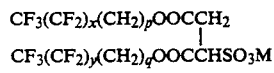

where
M is a cation,
x and y are each independently 0 or an integer of from 1 to 6 such that the sum of x and y is an integer of from 2 to 6,
p and q are each independently 1 or 2, with the proviso that when the sum of x and y is 6, p and q are each 1, and when the sum of x and y is 2, p and q are each 2.

The coating aids used in the present invention have the advantage that they reduce repellencies to a greater extent than prior art coating aids, especially those caused by external contaminants.

DESCRIPTION OF THE PREFERRED EMBODIMENTS

In one embodiment of the invention, the fluoroalkyl surface active agent has the formula:

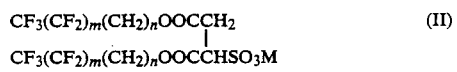

where
M is a cation,
m is an integer of from 1 to 3, and
n is 1 or 2,
with the proviso that if m=1, then n=2, and if m=3, then n=1.

In a preferred embodiment of formula (II), m is 2 and n is 1.

Examples of cations useful as M in the above formula include alkali metal ions derived from sodium, lithium, or potassium, ammonium groups such as tetraalkyl ammonium, ethanolamine, or diethanolamine, or other organic salts that do not render the compound insoluble in the coating medium.

Preferably, the coating aid is used in an amount from 0.01 to 0.3, and more preferably from 0.02 to 0.15, weight percent based on the weight of the hydrophilic colloid coating composition. The optimum concentration range for the coating aid depends on the source of the repellency and on whether other surface active agents are present.

The preferred hydrophilic colloid is gelatin (e.g., alkali-treated gelatin (cattle bone or hide gelatin) or acid-treated gelatin (pigskin gelatin)), or a gelatin derivative (e.g., acetylated gelatin or phthalated gelatin). Other hydrophilic colloids useful in the invention include naturally-occurring substances, such as proteins, protein derivatives, cellulose derivatives (e.g., cellulose esters) polysaccharides (e.g., dextran, gum arabic, zein, casein, and pectin), collagen derivatives, agar-agar, arrowroot, and albumin. The examples of synthetic hydrophilic colloids useful in the invention include polyvinyl alcohol, acrylamide polymers, maleic acid copolymers, acrylic acid copoylmers, methacrylic acid copolymers, and polyalkylene oxides.

The photographic composition of the invention may be used to coat any layer of a photographic element. Such layers are well-known in the art, and include silver halide emulsion layers, intermediate layers, antihalation layers, filter layers, antistatic layers, protective layers, and others as described in *Research Disclosure*, Item 17643, December, 1978 [hereinafter referred to as *Research Disclosure*], the disclosure of which is incorporated herein by reference. In a preferred embodiment, the composition of the invention is coated as a protective overcoat of a photographic element.

The material of this invention may comprise a negative-working or positive-working silver halide emulsion layer. Suitable emulsions and their preparation are described in *Research Disclosure* Section I and II and the publications cited therein. Suitable vehicles for the emulsion layers and other layers of elements of this invention are described in *Research Disclosure* Section IX and the publications cited therein.

For color photographic materials, references giving information on couplers and on methods for their dispersion are given in Sections VII and XIV, respectively, of *Research Disclosure*. An account of dye-forming development is given in 'Modern Photographic Processing', Vol. 2, Grant Haist, Wiley, N.Y., 1978, Chapter 9.

The photographic materials of this invention, or individual layers thereof, can contain brighteners (see *Research Disclosure* Section V), antifoggants and stabilizers (see *Research Disclosure* Section VI), antistain agents and image dye stabilizers (see Research Disclosure Section VII, paragraphs I and J), light absorbing and scattering materials (see *Research Disclosure* Section VIII, hardeners (see *Research Disclosure* Section XI), plasticizers and lubricants (see *Research Disclosure* Section XII), antistatic agents (see *Research Disclosure* Section XIII), matting agents (see *Research Disclosure* Section XVI), and development modifiers (see *Research Disclosure* Section XXI).

The photographic materials can be coated on a variety of supports as described in *Research Disclosure* section VII and the references described therein.

The photographic materials can be exposed to actinic radiation, typically in the visible region of the spectrum, to form a latent image as described in *Research Disclosure* Section XVIII and then processed to form a visible dye image as described in *Research Disclosure* Section XIX. Processing to form a visible dye image includes the step of contacting the element with a color developing agent to reduce developable silver halide and oxidize the color developing agent. Oxidized color developing agent in turn reacts with the coupler to yield a dye.

Development is followed by the conventional steps of bleaching, fixing, or bleach-fixing, to remove silver and silver halide, washing and drying.

Methods of synthesizing difluoroalkyl sulfosuccinates are known. In order to prepare a coating aid for use in the present invention, an appropriate fluoroalcohol can be reacted with fumaryl chloride in the presence of a base to give the corresponding difluoroalkyl fumarate or or it can be reacted with maleic anhydride in the presence of an acid to give the difluoroalkyl maleate. Difluoroalkyl fumarates and difluoroalkyl maleates both yield sodium difluoroalkyl sulfosuccinate when treated with sodium metabisulphite. An example of the preparation of a coating aid used in the invention is given below.

Preparation of sodium diheptafluorobutyl sulfosuccinate

Fumaryl chloride (18.36 g, 0.12 mol) was added dropwise to a stirred solution of 1H,1H -heptafluorobutan-1-ol (48.00 g, 0.24 mol) and dimethylaniline (30.43 ml, 0.24 mol) in tetrahydrofuran (300 ml) under a nitrogen atmosphere. The temperature was maintained at 20° to 25° C. The dark maroon solution was stirred for 1 hour, then refluxed for 7 hours. Water (500 ml) and diethyl ether (400 ml) were added. The mixture was shaken and the organic phase separated. The ethereal extracts were washed with 10% sulphuric acid (3×100 ml) and then with saturated aqueous sodium hydrogen carbonate (1×150 ml). The extracts were dried over anhydrous magnesium sulphate, filtered and evaporated at reduced pressure to give a crude brown oil. Vacuum distillation provided diheptafluorobutyl fumarate as a colorless liquid that crystallized on cooling. Yield: 42.89 g (75%); b.p. 82°-92° C. (0.4 torr).

Diheptafluorobutyl fumarate (12.60 g, 0.026 mol) was dissolved in ethanol (200 ml). Water (50 ml) and sodium metabisulphite (5.50 g, 0.029 mol) were added and the mixture refluxed for a total of 5 hours. During the first hour, sodium sulphite (3.00 g, 0.024 mol) was added in portions. The resulting solution was cooled and the ethanol removed at reduced pressure. Water (200 ml) was added and the aqueous emulsion extracted with ethyl acetate (3×150 ml). The extracts were dried over anhydrous magnesium sulphate, filtered, and evaporated under reduced pressure to give a white solid. Yield 10.1 g (66%).

Analytical and spectroscopic data showed that the solid was sodium diheptafluorobutyl sulfosuccinate.

The invention is further illustrated by the following Examples.

| ROOCCH$_2$ |  |
|---|---|
| ROOCCHSO$_3$M | |
| Compound 1 (invention): | R = C$_3$F$_7$CH$_2$— |
| Compound 2 (Comparison): | R = H(CF$_2$)$_4$CH$_2$— |
| Compound 3 (Comparison): | R = CF$_3$(CF$_2$)$_3$(CH$_2$)$_2$— |
| Compound 4 (Comparison): | R = C$_2$F$_5$CH$_2$— |
| Compound 5 (Comparison): | R = H(CF$_2$)$_2$CH$_2$— |

EXAMPLE 1

The ability of a coating aid to control repellencies caused by an impurity often found in hydrophilic colloid coating compositions was tested as follows.

Two gelatin layers, the uppermost of which contained sodium diheptafluorobutyl sulfosuccinate as a coating aid, were coated onto a polyethylene terephthalate film base subbed to give good adhesion to gelatin. The bottom layer consisted of a 4% by weight solution of lime-processed bone gelatin in water coated at 85.4 ml/m$^2$. The top layer consisted of a 7% by weight solution of lime-processed bone gelatin in water containing a colored dye marker, 1 ppm oleic acid emulsified in small droplet form to induce repellency sodium diheptafluorobutyl sulfocuccinate of concentrations indicated in Table I. The top layer was applied at a coverage of 14.2 ml/m$^2$. Both layers were applied simultaneously at a temperature of 40° C. using a conventional double slide hopper with applied suction and a linear coating speed of 15.25 m/min. In a separate series of experiments, the coatings were repeated using a linear coating speed of 30.5 m/min.

For each series of experiments, the coating aid was used in amounts ranging from 0.01 to 0.20% by weight. In each case, the coating was uniform and free from repellencies.

For comparison, the experiment was repeated using compounds 3 and 4, which fall outside the scope of the invention.

The results are summarized in Table I below.

TABLE I

| Coating Aid | Concn (wt. %) | Coating Result |
| --- | --- | --- |
| 1 (invention R=$C_3F_7CH_2$) | 0.02 | No repellencies |
| | 0.05 | No repellencies |
| 3 (comparison R=$C_4F_9(CH_2)_2$) | 0.02 | Many repellencies |
| | 0.05 | Many repellencies |
| 4 (comparison R=$C_2F_5CH_2$) | 0.02 | Many repellencies |
| | 0.05 | Many repellencies |

The results in Table I show the superiority of the compound used in the invention for controlling repellencies over the comparison compounds.

EXAMPLE 2

The ability of a coating aid to control repellencies caused by surface active material of the type often introduced by an external source during the coating process was tested as follows. In this Example, the coating comprised two layers and the coating aid material was present at the same concentration throughout the coating.

The gelatin layers were coated following the procedure of Example 1. The layers had the same composition as described in Example 1 except no oleic acid was added and an amount of sodium heptafluorobutyl sulfosuccinate or comparison compound equal to the amount present in the top layer was added to the lower layer.

A small amount of a non-ionic surface active agent solution (25% by weight in water) representing a contaminant was introduced directly onto the top layer by touching it onto the surface using a platinum loop-shaped wire. A series of non-ionic surface active agent solutions, each having a slightly different surface activity measured independently with a surface tensioniometer by the Wilhelmy plate method, was applied to the surface of the top layer.

By examining which surface active contaminants produced repellencies in the coating and which did not, a measure was obtained of the extent to which the coating aid provided protection against repellencies from an external source.

In this Example, the solutions of compounds representing the contaminant were applied to the coated layers at approximately 15 cm from where the layers were applied to the support. For comparison, a compound similar in structure to those suitable for use in the present invention was also tested. The results are shown in Table II.

TABLE II

| Coating Aid | Concn. (wt. %) | Surface Tension Minimum (mN/m) produced by Contaminant | | | | | | | |
| --- | --- | --- | --- | --- | --- | --- | --- | --- | --- |
| | | 18 | 22 | 24 | 26.5 | 29 | 31 | 43 | 46.5 |
| 1 (invention R=$C_3H_7CH_2$) | 0.05 | R | C | C | C | C | C | — | — |
| | 0.10 | R | C | C | C | C | C | — | — |
| 2 (comparison R=$H(CF_2)_4CH_2$) | 0.05 | R | R | R | R | R | R | — | — |
| | 0.10 | R | R | R | R | C | C | — | — |
| 5 (comparison R=$H(CF_2)_2CH_2$) | 0.05 | — | — | — | — | — | — | R | R |
| | 0.10 | — | — | — | — | — | — | R | R |

In Table II, R denotes that the surface-active contaminant produces a repellency while C denotes that no repellency is produced, i.e., repellency formation has been controlled.

The above results clearly demonstrate the extra protection against external sources of repellency provided by a coating aid used in the invention relative to the comparison compounds. Compound 2 required higher concentrations than the compound of the invention to control the formation of repellencies. Compound 5 did not control repellencies even when used at higher concentrations than the compound of the invention.

EXAMPLE 3

The ability of a coating aid to control repellencies arising from surface active material introduced by an external source during the coating process was tested as follows. In this Example, the coating comprises two layers and the coating aid was present in the top layer of the coating only.

Two gelatin layers were coated following the procedure of Example 1. Then a series of non-ionic surface active agent solutions were applied to the surface of the coating in the same manner as described in Example 2. The results of the experiments are presented in Table III.

TABLE III

| Coating Aid | Concn. (wt. %) | Surface tension minimum produced by contaminant (mN/m) | | | | | | | |
| --- | --- | --- | --- | --- | --- | --- | --- | --- | --- |
| | | 24 | 26.5 | 29 | 31 | 34 | 36 | 43 | 46.5 |
| 1 (invention R=$C_3H_7CH_2$) | 0.13 | R | C | C | C | C | C | — | — |
| 2 (comparison R=$H(CF_2)_4CH_2$) | 0.13 | R | R | R | R | R | C | — | — |
| 5 (comparison R=$H(CF_2)_2CH_2$) | 0.13 | — | — | — | — | — | — | R | R |

As before, R denotes that the surface active contaminant produces a repellency while C denotes that no repellency is produced.

These results clearly demonstrate the extra protection against external sources of repellency provided by a coating aid used in the invention relative to the comparison compounds. Compound 2 required higher concentrations than the compound of the invention to control the formation of repellencies. Compound 5 did not control repellencies even when used at higher concentrations than the compound of the invention.

EXAMPLE 4

The ability of a coating aid to control repellencies arising from a surface-active lubricant and a surface-active antifoam agent arriving at the surface during coating was tested as follows.

Two gelatin layers were coated following the procedure of Example 1. The layers had the same composition as described in Example 1 except that in some cases the coating aid was added to the bottom layer such that its concentration matched that of the top layer.

A small amount of a lubricant WD40 ®, sold by the WD40 Co., Ltd., United Kingdom and an antifoam agent, Nalco 2341 ®, sold by the Nalco Chemical Co., Illinois, were introduced individually onto the top layer using the same method as that employed in Example 2. By examining which coatings exhibited repellency and which did not, a measure was obtained of the relative ability of the coating aid to provide protection against the two surface-active contaminants.

Results of the experiments performed are shown in Table IV.

TABLE IV

| Coating Aid | Concentration of Coating Aid (wt. %) | | Contaminant | |
|---|---|---|---|---|
| | bottom layer | top layer | WD40 ® | Nalco 2341 ® |
| 1 | 0.05 | 0.05 | C | C |
| (invention | 0.10 | 0.10 | C | C |
| R=C$_3$F$_7$CH$_2$) | 0 | 0.13 | C | C |
| | 0 | 0.20 | C | C |
| | 0 | 0.25 | C | C |
| 2 | 0 | 0.13 | R | R |
| (comparison | 0 | 0.20 | R | R |
| R=H(CF$_2$)$_4$CH$_2$) | 0 | 0.25 | R | R |
| 5 | 0.05 | 0.5 | R | R |
| (comparison | 0.10 | 0.10 | R | R |
| R=H(CF$_2$)$_2$CH$_2$) | 0 | 0.13 | R | R |
| | 0 | 0.20 | R | R |
| | 0 | 0.25 | R | R |

As in the previous Examples, these results clearly demonstrate the extra protection afforded by a coating aid of this invention relative to the comparison compounds.

The invention has been described in detail with particular reference to preferred embodiments thereof, but it will be understood that variations and modifications can be effected within the spirit and scope of the invention.

What is claimed is:

1. A photographic element comprising a support having thereon a layer comprising a hydrophilic colloid and a compound of the formula:

$$CF_3(CF_2)_2CH_2OOCCH_2$$
$$|$$
$$CF_3(CF_2)_2CH_2OOCCHSO_3M$$

wherein M is cation, and wherein said compound is present in an amount of 0.01 to 0.3 weight percent based on the weight of the hydrophilic colloid.

2. A photographic element according to claim 1 wherein the compound is present in an amount of 0.02 to 0.15 weight percent based on the weight of the hydrophilic colloid.

3. A photographic element according to claim 1 wherein said layer is the outermost layer of the element.

4. A photographic element according to claim 1 wherein the hydrophilic colloid is gelatin.

5. A photographic element according to claim 4 wherein said layer is the outermost layer of the element.

6. The photographic element of claim 1 wherein said element comprises silver halide.

7. A photographic element according to claim 6 wherein the hydrophilic colloid is gelatin.

8. A photographic element comprising silver halide and comprising a support having thereon a layer comprising gelatin and a compound of the formula:

$$CF_3(CF_2)_2CH_2OOCCH_2$$
$$|$$
$$CF_3(CF_2)_2CH_2OOCCHSO_3M$$

wherein M is cation, and wherein said compound is present in an amount of 0.01 to 0.3 weight percent based on the weight of the gelatin.

* * * * *